United States Patent

Seele et al.

[11] Patent Number: 5,179,114
[45] Date of Patent: Jan. 12, 1993

[54] α-HYDROXYAZOLYLETHYLOXIRANES AND FUNGICIDES CONTAINING THESE COMPOUNDS

[75] Inventors: Rainer Seele; Reiner Kober, both of Fussgoenheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 764,965

[22] Filed: Sep. 25, 1991

Related U.S. Application Data

[63] Continuation of Ser. No. 542,658, Jun. 25, 1990, abandoned, which is a continuation of Ser. No. 360,455, Jun. 2, 1989, abandoned.

[30] Foreign Application Priority Data

Jun. 4, 1988 [DE] Fed. Rep. of Germany ....... 3819053

[51] Int. Cl.$^5$ .................. A01N 43/653; C07D 249/08
[52] U.S. Cl. .................................... 514/383; 514/184; 548/267.2; 548/267.8; 548/268.6
[58] Field of Search ................ 514/383, 184; 548/267.2, 267.8, 268.6, 101

[56] References Cited

FOREIGN PATENT DOCUMENTS 251086 1/1988 European Pat. Off. ............ 548/262
1318590 12/1970 United Kingdom .

Primary Examiner—Patricia L. Morris
Attorney, Agent, or Firm—Oblon, Spivak, McClelland, Maier & Neustadt

[57] ABSTRACT

α-Hydroxyazolylethyloxiranes of the general formula I

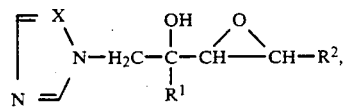

where $R^1$ and $R^2$ are each alkyl, cycloalkyl, cycloalkenyl, phenyl, biphenyl, naphthyl or pyridyl, these radicals being unsubstituted or substituted, and X is CH or N, their plant-tolerated acid addition salts and metal complexes, and fungicides containing these compounds.

13 Claims, No Drawings

α-HYDROXYAZOLYLETHYLOXIRANES AND FUNGICIDES CONTAINING THESE COMPOUNDS

This application is a Continuation of application Ser. No. 07/542,658, filed on June 25, 1990, now abandoned, which is a continuation of Ser. No. 07/360,455, filed on June 2, 1989, now abandoned.

The present invention relates to novel azole compounds, processes for their preparation and fungicides containing these compounds.

It is known that 1-[2-(2,4-dichlorophenyl)-2-(2-propenyloxy)-ethyl]-1H-imidazole can be used as a fungicide (GB-1 318 590).

We have found that α-hydroxyazolylethyloxiranes of the general formula I

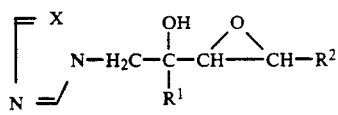

where $R^1$ and $R^2$ are each alkyl, cycloalkyl, cycloalkenyl, phenyl, biphenyl, naphthyl or pyridyl, these radicals being unsubstituted or substituted by halogen, nitro, amino, phenoxy, alkyl, alkoxy or haloalkyl, each of 1 to 4 carbon atoms, and X is CH or N, and their plant-tolerated acid addition salts or metal complexes have a better fungicidal action, in particular against cereal diseases, than known azole compounds.

The compounds of the formula I may have a cis or trans configuration with respect to the oxirane radical. The trans compounds are preferred.

The compounds of the formula I contain asymmetric carbon atoms and can therefore occur as enantiomers and diastereomers. The invention embraces both the pure isomers and their mixtures. The mixtures of diastereomers can be separated into the components by known methods, for example by fractional crystallization from suitable solvents or by chromatography over silica gel. In the case of the novel compounds, the racemates can be resolved by conventional methods, for example by salt formation with an optically active acid, separation of the diastereomeric salts and liberation of the enantiomers by means of a base. Both the pure isomers and their mixtures formed in the preparation are suitable for use as fungicides. The mixtures are preferred.

$R^1$ and $R^2$ are each, for example, branched or straight-chain, unsubstituted or substituted $C_1$–$C_{12}$-alkyl, in particular $C_1$–$C_5$-alkyl, such as methyl, ethyl, isopropyl, n-propyl, n-butyl, isobutyl, sec-butyl, tert-butyl, n-pentyl or neopentyl, particularly suitable substituents being halogen, for example chlorine or fluorine, eg. trifluoromethyl or trichloromethyl; $C_3$–$C_6$-cycloalkyl or cycloalkenyl, such as cyclopropyl, cyclobutyl, cyclopentyl, cyclohexyl, 2-cyclohexenyl or 3-cyclohexenyl, and phenyl, biphenyl, naphthyl or pyridyl, in particular phenyl, the aromatic radicals being unsubstituted or carrying one or more, for example 1-3, substituents, such as halogen, eg. bromine, chlorine or fluorine, nitro, amino, phenoxy, $C_1$–$C_4$-alkyl, $C_1$–$C_4$-alkoxy or $C_1$–$C_4$-halo alkyl, eg. fluoro- or chloroalkyl having 1 to 3 halogen atoms; the following radicals are examples: phenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, 2-methoxyphenyl, 3-methoxyphenyl 4-methoxyphenyl, 2,4-dimethoxyphenyl, 4-ethylphenyl, 4-isopropylene, 4-tert-butylphenyl, 4-tert-butyoxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-trifluoromethylphenyl, 3-trifluoromethylphenyl) 1,4-trifluoromethylphenyl,cyclopropyl, cyclobutyl, cyclopentyl, cyclohexyl, cyclooctyl, 2-cyclohexenyl and 3-cyclohexenyl.

Acid addition salts are, for example, the hydrochlorides, bromides, sulfates, nitrates, phosphates, oxalates and dodecylbenzenesulfonates. The activity of the salts is attributable to the cation, so that in general the anion is unimportant. The novel active ingredient salts are prepared by reacting the trans-α-hydroxyazolylethyloxiranes (I) with acids.

Metal complexes of the active ingredients I or of their salts can be formed with copper, zinc, tin, manganese, iron, cobalt or nickel by reacting the trans-α-hydroxyazolylethyloxiranes with the corresponding metal salts, for example with copper sulfate, zinc chloride or tin chloride.

The compounds of the formula I can be prepared by reacting a compound of the formula II

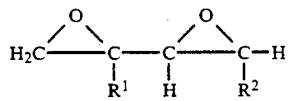

where $R^1$ and $R^2$ have the stated meanings, with a compound of the formula III

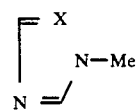

where Me is a halogen atom or a metal atom and X has the stated meanings, in the presence of a base.

Where Me is a hydrogen atom, the reaction is carried out in the presence or absence of a solvent or diluent, with or without the addition of a reaction accelerator at from 10° to 150° C., in particular from 20° to 120° C. The preferred solvents and diluents include ketones, such as acetone, methyl ethyl ketone or cyclohexanone, nitriles, such as acetonitrile or propionitrile, alcohols, such as methanol, ethanol, isopropanol, n-butanol or glycol, esters, such as ethyl acetate, methyl acetate or butyl acetate, ethers, such as tetrahydrofuran, diethyl ether, dimethoxyethane, dioxane or diisopropyl ether, amides, such as dimethylformamide, dimethylacetamide or N-methylpyrrolidone, and dimethyl sulfoxide, sulfolane and mixtures of these.

Examples of suitable bases, which may furthermore be used as acid acceptors in the reaction, are alkali metal hydroxi-des, such as sodium hydroxide or potassium hydroxide, and carbonates, such as lithium carbonate, sodium carbonate or cesium carbonate or sodium bicarbonate, potassium bicarbonate or cesium bicarbonate, pyridine and 4-dimethylaminopyridine. However, it is also possible to use other conventional bases.

Preferred reaction accelerators are metal halides, such as sodium iodide or potassium iodide, quaternary ammonium salts, such as tetrabutylammonium chloride, bromide, iodide or hydrogen sulfate, benzyltriethylammonium chloride or bromide, and crown ethers, such as 12-crown-4, 15-crown-5-18-crown-6, dibenzo-18-crown-6- or dicyclohexano-18-crown-6.

The reaction is carried out in general under atmospheric or superatmospheric pressure, continuously or batchwise, by a conventional method.

If Me is a metal atom, the reaction is carried out in the presence or absence of a solvent or diluent and with or without the addition of a strong inorganic or organic base, at from −10° to 120° C. The preferred solvents and diluents include amides, such as dimethylformamide, diethylformamide, dimethylacetamide, diethylacetamide, N-methylpyrrolidone or hexamethylphosphorotriamide, sulfoxides, such as dimethyl sulfoxide, and finally sulfolane.

Examples of suitable bases, which may furthermore be used as acid acceptors in the reaction, are alkali metal hydrides, such as lithium hydride, sodium hydride or potassium hydride, alkali metal amides, such as sodium amide or potassium amide, and sodium tert-butoxide, potassium tert-butoxide, triphenylmethyllithium, triphenylmethylsodium, triphenylmethylpotassium, naphthalenelithium, naphthalenesodium and naphthalenepotassium.

The reaction is carried out in general at from 0° to 100° C., preferably from 20° to 80°. When a solvent is present, the reaction is advantageously effected at the boiling point of the particular solvent.

For the preparation of the novel compounds I by the methods described above, the starting materials are usually used in a stoichiometric ratio. An excess of one or other of the components (not more than 10%) may be advantageous.

Usually, not less than equivalent amounts, based on III, of the base are added, although an excess of the base may also be used.

The novel starting compounds II can be prepared by a conventional method, in a simple manner, from an oxirane of the formula IV

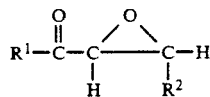

for example by reaction with trimethylsulfonium methylsulfate (cf. Corey and Chaykovsky, J. Amer. Chem. Soc. 64 (1962), 3782 et seq.).

The epoxides IV can be prepared from the olefins V by known processes. For this purpose, an olefin V

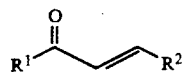

is oxidized with a heroxycarboxylic acid, suoh as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid, in an inert solvent, preferably a chlorohydrocarbon, eg. methylene chloride, chloroform, carbon tetrachloride or dichloroethane, or, if necessary, in acetic acid, ethyl acetate, acetone or dimethylformamide, in the presence or absence of a buffer, such as sodium acetate, sodium carbonate, disodium hydrogen phosphate or Triton B. The reaction is carried out at from 10° to 100° C. and may be catalyzed, for example, with iodine, sodium tungstate or light. The oxidation can also be carried out using an alkaline solution of hydrogen peroxide (about 30%) in methanol, ethanol, acetone or acetonitrile at from 25° to 30° C. or an alkyl hyiroperoxide, eg. tert-butyl hydroperoxide, with the addition of a catalyst, eg. sodium tungstate, pertungstic acid, molybdenum hexacarbonyl or vanadyl acetylacetonate. Some of the stated oxidizing agents can be produced in situ.

The corresponding cis compounds can be prepared by isomerization of the trans compounds in a conventional manner, as described in, for example, European Patent 240,216.

The compounds V can be prepared by generally known processes for olefin synthesis (Houben-Weyl-Müller, Methoden der organischen Chemie, Georg Thieme Verlag, Stuttgart, 1972, Vol. V, 1b).

The Examples which follow illustrate the preparation of the active ingredients.

I. Preparation of the starting materials

Method A 98.2 g of E-phenyl 2-chlorophenylstyryl ketone are dissolved in 300 ml of methanol, and 8 ml of 50% strength sodium hydroxide solution are added. The reaction solution is stirred at 0° C. while 30.3 g of about 50% strength hydrogen peroxide are slowly added dropwise, the internal temperature not exceeding 30° C. Thereafter, the reaction mixture is stirred for six hours at room temperature (20° C.) and is worked up by adding 50 ml of water to the solution and filtering off the resulting precipitate under suction. 94.6 g (90%) of 2-benzoyl-3-(2-chlorophenyl)-oxirane of melting point 132° C. are obtained.

Method B 28 g of trimethylsulfonium methylsulfate and 70 ml of 50% strength sodium hydroxide solution are added to a solution of 39 g of 2-benzoyl-3-(2-chlorophenyl)oxirane in 250 ml of methylene chloride. The reaction mixture is kept at room temperature for from 12 to 15 hours, after which 200 ml of water are added to the solution and the organic phase is separated off. The remaining aqueous phase is extracted with methylene chloride, and the combined organic phases are washed with water, dried over sodium sulfate and evaporated down to give 34 g (83%) of2-[(2-phenyl)-oxiran-2-yl]-3-(2-chlorophenyl)oxirane, which is reacted with triazole in the f Example, without further purification.

II. Preparation of the end products

EXAMPLE 1

9.4 g of potassium carbonate are added to a solution of 3.7 g of triazole in 50 ml of N-methylpyrrolidone, after which 11.2 g of 2-[(2-phenyl)-oxiran-2-3-(2-chlorophenyl)-oxirane, dissolved in 50 ml of N-methylpyrrolidone, are slowly added dropwise at room temperature. After the reaction mixture has been stirred for from 10 to 18 hours at room temperature, 100 ml of water are added to the solution and the mixture is extracted several times by shaking with methyl tert-butyl ether. The organic phase isolated is washed with water, dried over sodium sulfate and evaporated down. Crystallization of the remaining residue from methyl tert-butyl ether/n- hexane gives 8.1 g (58%) of trans-2-[1-hydroxy-1-phenyl-2(1,2,4-triazol-1-yl) -ethyl]-3-(2-chlorophenyl)-oxirane of melting point 180°-182° C. (compound No. 1).

The compounds given in the table below may be prepared analogously to Example 1.

In general terms, the novel compounds are extremely effective on a broad spectrum of phytopathogenic fungi, in particular those from the Ascomycetes and Basidiomycetes classes. Some of them have a systemic action and can be used as foliar and soil fungicides.

TABLE

Trans-α-hydroxy-azolylethyloxiranes

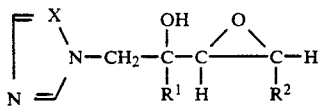

| Example | R$^1$ | R$^2$ | X | m.p./IR | Comments |
|---|---|---|---|---|---|
| 1 | C$_6$H$_5$ | 2-Cl—C$_6$H$_4$ | N | 180–182° C. | enantiomer mixture |
| 2 | C$_6$H$_5$ | 2-Cl—C$_6$H$_4$ | CH | — | — |
| 3 | C$_6$H$_5$ | 4-Cl—C$_6$H$_4$ | N | — | — |
| 4 | C$_6$H$_5$ | 4-F—C$_6$H$_4$ | N | — | — |
| 5 | C$_6$H$_5$ | 2,4-Cl$_2$—C$_6$H$_3$ | N | — | — |
| 6 | C$_6$H$_5$ | 2-Cl-4-F—C$_6$H$_3$ | N | — | — |
| 7 | C$_6$H$_5$ | 3-NO$_2$—C$_6$H$_4$ | N | — | — |
| 8 | C$_6$H$_5$ | 4-NH$_2$—C$_6$H$_4$ | N | — | — |
| 9 | C$_6$H$_5$ | 2-OCH$_3$—C$_6$H$_4$ | N | — | — |
| 10 | C$_6$H$_5$ | 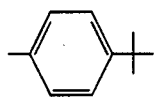 | N | 179–180° C. | enantiomer mixture |
| 11 | C$_6$H$_5$ | cyclohexyl | N | — | — |
| 12 | C$_6$H$_5$ | cyclohexyl | CH | — | — |
| 13 | C$_6$H$_5$ | 3-cyclohexenyl | N | — | — |
| 14 | 4-Cl—C$_6$H$_4$ | C$_6$H$_5$ | N | 121° C. | D$_1$:D$_2$ = 2:1 |
| 15 | 4-Cl—C$_6$H$_4$ | 2-Cl—C$_6$H$_4$ | N | 208–210° C. | enantiomer mixture |
| 16 | 4-Cl—C$_6$H$_4$ | 2-Cl—C$_6$H$_4$ | CH | 170° C. | enantiomer mixture |
| 17 | 4-Cl—C$_6$H$_4$ | 4-Cl—C$_6$H$_4$ | N | — | — |
| 18 | 4-Cl—C$_6$H$_4$ | 4-Cl—C$_6$H$_4$ | CH | — | — |
| 19 | 4-Cl—C$_6$H$_4$ | 2-F—C$_6$H$_4$ | N | 125–127° C. | D$_1$:D$_2$ = 1.2:1 |
| 20 | 4-Cl—C$_6$H$_4$ | 4-F—C$_6$H$_4$ | N | resin | D$_1$:D$_2$ = 1.2:1 |
| 21 | 4-Cl—C$_6$H$_4$ | 4-F—C$_6$H$_4$ | CH | — | — |
| 22 | 4-Cl—C$_6$H$_4$ | 2,4-Cl$_2$—C$_6$H$_3$ | N | — | — |
| 23 | 4-Cl—C$_6$H$_4$ | 2-Cl-4-F—C$_6$H$_3$ | N | — | — |
| 24 | 4-Cl—C$_6$H$_4$ | cyclohexyl | N | — | — |
| 25 | 4-Cl—C$_6$H$_4$ | cyclohexyl | CH | — | — |
| 26 | 4-Cl—C$_6$H$_4$ | 3-cyclohexenyl | N | — | — |
| 27 | 4-F—C$_6$H$_4$ | 2-Cl—C$_6$H$_4$ | N | 192–193° C. | enantiomer mixture |
| 28 | 4-F—C$_6$H$_4$ | 2-Cl—C$_6$H$_4$ | CH | 150° C. | enantiomer mixture |
| 29 | 4-F—C$_6$H$_4$ | 4-Cl—C$_6$H$_4$ | N | — | — |
| 30 | 4-F—C$_6$H$_4$ | 4-Cl—C$_6$H$_4$ | CH | — | — |
| 31 | 4-F—C$_6$H$_4$ | 2-F—C$_6$H$_4$ | N | — | — |
| 32 | 4-F—C$_6$H$_4$ | 4-F—C$_6$H$_4$ | N | — | — |
| 33 | 4-F—C$_6$H$_4$ | 2,4-Cl$_2$—C$_6$H$_3$ | N | — | — |
| 34 | 4-F—C$_6$H$_4$ | 2-OCH$_3$—C$_6$H$_4$ | N | — | — |
| 35 | 4-F—C$_6$H$_4$ | cyclohexyl | N | — | — |
| 36 | 4-OCH$_3$—C$_6$H$_4$ | 2-Cl—C$_6$H$_4$ | N | — | — |
| 37 | 4-OCH$_3$—C$_6$H$_4$ | 4-Cl—C$_6$H$_4$ | N | — | — |
| 38 | 4-OCH$_3$—C$_6$H$_4$ | 4-F—C$_6$H$_4$ | N | — | — |
| 39 | 4-OCH$_3$—C$_6$H$_4$ | 2-Cl-4-F—C$_6$H$_3$ | N | — | — |
| 40 | 4-OCH$_3$—C$_6$H$_4$ | 2-OCH$_3$—C$_6$H$_4$ | N | — | — |
| 41 | cyclopropyl | 2-Cl—C$_6$H$_4$ | N | resin | D$_1$:D$_2$ = 1.3:1 |
| 42 | cyclopropyl | 2-Cl—C$_6$H$_4$ | CH | — | — |
| 43 | cyclopropyl | 4-Cl—C$_6$H$_4$ | N | 170–172° C. | enantiomer mixture |
| 44 | cyclopropyl | 2-F—C$_6$H$_4$ | N | — | — |
| 45 | cyclopropyl | 4-F—C$_6$H$_4$ | N | 130–133° C. | enantiomer mixture |
| 46 | cyclopropyl | 2,4-Cl$_2$—C$_6$H$_3$ | CH | — | — |
| 47 | cyclopropyl | cyclohexyl | N | — | — |
| 48 | cyclopropyl | 3-cyclohexenyl | N | — | — |
| 49 | cyclohexyl | 2-Cl—C$_6$H$_4$ | N | 238–246° C. | enantiomer mixture |
| 50 | cyclohexyl | 2-Cl—C$_6$H$_4$ | CH | — | — |
| 51 | cyclohexyl | 4-Cl—C$_6$H$_4$ | N | — | — |
| 52 | cyclohexyl | 2-F—C$_6$H$_4$ | N | — | — |
| 53 | cyclohexyl | 4-F—C$_6$H$_4$ | N | 160° C. | enantiomer mixture |
| 54 | cyclohexyl | cyclohexyl | N | — | — |
| 55 | C$_3$H$_7$ | 2-Cl—C$_6$H$_4$ | N | — | — |
| 56 | C$_3$H$_7$ | 2-Cl—C$_6$H$_4$ | CH | — | — |
| 57 | C$_3$H$_7$ | cyclohexyl | N | — | — |
| 58 | tert.-butyl | 4-Cl—C$_6$H$_4$ | N | 130° C. | enantiomer mixture |

D$_1$ = diastereomer 1    D$_2$ = Diastereomer 2

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horiculture and viticulture, and in vegetables such as cucumbers, beans and curcurbits.

The novel compounds are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns, Ustilago species in cereals and sugarcane,
Venturia inaequalis (scab) in apples,
Heiminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Vertifillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxilaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90 wt% of active ingredient. The application rates are from 0.02 to 3 kg or more of active ingredient per hectare, depending on the type of effect desired. The novel compounds may also be used for protecting materials, e.g., against Paecilomyces variotil.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 15 is mixed with 10 parts by weight of N-methyl-α-pyrrolidone. A mixture is obtained which is suitable for application in the form of very fine drops.

II. 20 parts by weight of compound no. 19 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 49 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 53 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 15 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 19 is intimately mixed with 97 parts by weight of particulate kaolin. A dust is obtained containing 3% by weight of the active ingredient.

VII. 30 parts by weight of compound no. 49 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 53 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 15 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers.

Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
  sulfur
  dithiocarbamates and their derivatives, such as
  ferric dimethyldithiocarbamate
  zinc dimethyldithiocarbamate,
  zinc ethylenebisdithiocarbamate,
  manganese ethylenebisdithiocarbamate,
  manganese zinc ethylenediaminebisdithiocarbamate,
  tetramethylthiuram disulfides,
  ammonia complex of zinc N,N'-ethylenebisdithiocarbamate,
  ammonia complex of zinc N,N'-propylenebisdithiocarbamate,
  zinc N,N'-propylenebisdithiocarbamate and
  N,N'-polypropylenebis(thiocarbamyl) disulfide;
  nitro derivatives, such as
  dinitro(1-methylheptyl)-phenyl crotonate,
  2-sec-butyl-4,6-dinitrophenyl 3,3-dimethylacrylate,
  2-sec-butyl-4,6-dinitrophenyl isopropylcarbonate and
  diisopropyl 5-nitroisophthalate;
  heterocyclic substances, such as
  2-heptadecylimidazol-2-yl acetate,
  2,4-dichloro-6-(o-chloroanilino)-s-triazine,
  O,O-diethyl phthalimidophosphonothioate,
  5-amino-1-[-bis-(dimethylamino)-phosphinyl]-3-phenyl-1,2,4-triazole,
  2,3-dicyano-1,4-dithioanthraquinone,
  2-thio-1,3-dithio[4,5-]quinoxaline,
  methyl 1-(butylcarbamyl)-2-benzimidazolecarbamate,
  2-methoxycarbonylaminobenzimidazole,
  2-(fur-2-yl)-benzimidazole,
  2-(thiazole-4-yl)benzimidazole,
  N-(1,1,2,2-tetrachloroethylthio)-tetrahydrophthalimide,
  N-trichloromethylthiotetrahydrophthalimide,
  N-trichloromethylthiophthalimide,
  N-dichlorofluoromethylthio-N', N'-dimethyl-N-phenylsulfuric acid diamide,
  5-ethoxy-3-trichloromethyl-1,2,3-thiadiazole,
  2,-thiocyanatomethylthiobenzothiazole,
  1,4-dichloro-2,5-dimethoxybenzene,
  4-(2-chlorophenylhydrazono)-3-methyl-5-isoxazolone,
  2-thiopyridine 1-oxide,
  8-hydroxyquinoline and its copper salt,
  2,3-dihydro-5-carboxanilido-6-methyl-1,4-oxathiyne,
  2,3-dihydro-5-carboxanilido-6-methyl-1,4-4,4-dioxide,
  2-methylfuran-3-carboxanilide,
  2,5-dimethylfuran-3-carboxanilide,
  2,4,5-trimethylfuran-3-carboxanilide,
  2,5-dimethyl-N-cyclohexylfuran-3-carboxamide,
  N-cyclohexyl-N-methoxy-2,5-diethylfuran-3-carboxamide,
  2-methylbenzanilide,
  2-iodobenzanilide,
  N-formyl-N-morpholine-2,2,2-trichloroethylacetal,
  piperazine-1,4-diylbis-(1-(2,2,2-trichloroethyl)-formamide),
  1-(3,4-dichloroanilino)-1-formylamino-2,2,2-trichloroethane,
  2,6-dimethyl-N-tridecylmorpholine and its salts,
  2,6-dimethyl-N-cyclododecylmorpholine and its salts,
  N-[3-(p-tert.-butylphenyl)-2-methylpropyl]-cis-2,6-dimethylmorpholine,
  N-[3-(p-tert.-butylphenyl)-2-methylpropyl]-piperidine,
  1-[2-(2,4-dichlorophenyl)-4-ethyl-1,3-dioxolan-2-ylethyl]-1H-1,2,4-triazole,
  1-[2-(2,4-dichlorophenyl)-4-propyl-1,3-dioxolan-2-ylethyl]-1H-1,2,4-triazole,
  N-(n-propyl)-N-(2,4,6-trichlorophenoxyethyl)-N'-imidazolyl-urea,
  1-(4-chlorophenoxy)-3,3-dimethyl-1-(1H-1,2,4-triazol-1-yl)-butan-2-one,
  10(4-chlorophenoxy)-3,3-dimethyl-1-(1H-1,2,4-triazol-1-yl)-butan-2-ol,
  1-(4-phenylphenoxy)-3,3-dimethyl-1-(1H, 1,2,4-triazol-1)-2-butanol,
  α-(2-chlorophenyl)-α-(4-chlorophenyl)-5-pyrimidenemethanol,
  5-butyl-(2-dimethylamino-4-hydroxy-6-methyl-pyrimidine,
  bis-(p-chlorophenyl)-3-pyridinemethanol,
  1,2-bis-(3-ethoxycarbonyl-2-thioureido)-benzene,
  1,2-bis-(3-methoxycarbonyl-2-thioureido)-benzene,
  and various fungicides, such as
  dodecylquanidine acetate,
  3[3-(3,5-dimethyl-2-oxycyclohexyl-2-hydroxyethyl]-glutaramide, hexachlorobenzene,
  DL-methyl-N-(2,6-dimethylphenyl)-N-fur-2-yl alanate.
  methyl DL-N-(2,6-dimethylphenyl)-N-(2'-methoxyacetyl)-alanate,
  N-(2,6-dimethylphenyl)-N-chloroacetyl-DL-2-aminobutyrolactone,
  methyl DL-N-(2,6-dimethylphenyl)-N-(phenylacetyl)-alanate,
  5-methyl-5-vinyl-3-(3,5-dichlorophenyl)-2,4-dioxo-1,3-1,3-oxazolidine,
  3-[3,5-dichlorophenyl]-5-5-methoxymethyl-1,3-oxazolidine-2,4-dione,
  3-(3,5-dichlorophenyl)-1-isopropylcarbamylhydantoin,
  N-(3,5-dichlorophenyl)-1,2-dimethylcyclopropane-1,2-dicarboximide,
  2-cyano-[N-(ethylaminocarbonyl)-2-methoximinol]-acetamide,
  1-[2-(2,4-dichlorophenyl)-pentyl]-1H-1,2,4-triazole,
  2,4-difluoro-α-(1H-1,2,4-triazol-1-ylmethyl)-benzyhydryl alcohol,
  N-(3-chloro-2,6-dinitro-4-trifluoromethylphenyl)-5-trifluoromethyl-3-chloro-2-aminopyridine, and
  1-((bis-(4-fluorophenyl)-methylsilyl)-methyl-1H-1,2,4-triazole.

USE EXAMPLE

For comparison purposes, 1-[2-(2,4-dichlorophenyl)-2-(2-propenylloxy)ethyl]-1H-imidazole (A), an active ingredient disclosed in British 1,318,590, was used.

USE EXAMPLE 1

Action on wheat brown rust

Leaves of pot-grown wheat seedlings of the "Fruhgold" variety were dusted with spores of brown rust (Puccinia recodita). The pots were then placed for 24 hours at 20° to 22° C. in a high-humidity (90-95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 15, 19, 49 and 53, applied at 0.025 wt% spray liquors, had a better fungicidal action (97%) than prior art active ingredient A (80%).

We claim:

1. An α-Hydroxyazolylethylloxirane of the formula I

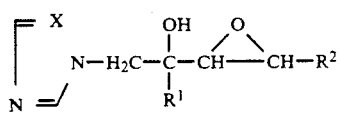

where $R^1$ and $R^2$ each $C_1$-$C_{12}$-alkyl, $C_3$-$C_6$-cycloalkyl, $C_3$-$C_6$-cycloalkenyl phenyl, biphenyl or naphthyl, these radicals being unsubstituted or substituted by halogen, nitro, amino, phenoxy, alkyl, alkoxy or haloalky, each of 1 to 4carbon atoms, at least one of $R^1$ and $R^2$ being $C_3$-$C_6$ cycloalkyl or $C_3$-$C_6$ cycloalkenyl, X is N, and their plant-tolerated acid addition salts or metal complexes.

2. A compound of the formula I as set forth in claim 1 and having a trans configuration with respect to the oxirane radical.

3. A fungicidal composition comprising a fungicidally effective amount of an α-hydroxyazolylethylethyloxirane of the formula I

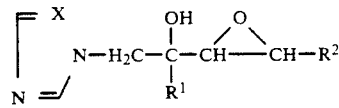

where $R^1$ and $R^2$ are each $R_1$-$C_{12}$-alkyl, $C_3$-$C_6$-cycloalkyl, $C_3$-$C_6$-cycloalkenyl phenyl, biphenyl or naphthyl, these radicals being unsubstituted or substituted by halogen, nitro, amino, phenoxy, alkyl, alkoxy or haloalkyl, each of 1 to 4 carbon atoms, at least one of $R^1$ and $R^2$ being $C_3$-$C_6$ cycloalkyl or $C_1$-$C_6$ cycloalkenyl, X is N, and their plant-tolerated acid addition salt or metal complex thereof, and an inert additive.

4. A process for combating fungi, wherein a fungicidally effective amount of an α-hydroxyazolylethyloxirane of the formula I

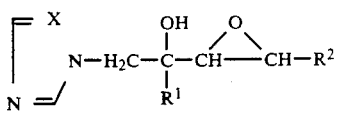

these radicals being unsubstituted or substituted by halogen, nitro, amino, phenoxy, alkyl, alkoxy or haloalkyl, each of 1 to 4carbon atoms, at least one of $R^1$ and $R^2$ being $C_3$-$C_6$ cycloalkyl or $C_3$-$C_6$ cycloalkenyl, X is N, and their plant-tolerated acid addition salt or metal complex thereof, is allowed to act on the fungi or on plants or seed threatened by fungus attack.

5. A compound of the formula I as set forth in claim 1, where $R^1$ is cyclohexyl and $R^2$ is 2-chlorophenyl, in trans configuration.

6. A compound of the formula I as set forth in claim 1, where $R^1$ is cyclohexyl and $R^2$ is 4-chlorophenyl in trans configuration.

7. A compound of the formula

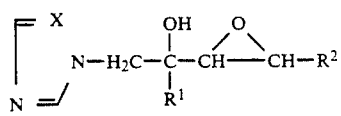

where $R^1$ is 4-chlorophenyl, $R^2$ is phenyl and X is N.

8. A fungicidal composition comprising a fungicidally effective amount of the compound of claim 7 and an inert additive.

9. A process for combating fungi, wherein a fungicidally effective amount of the compound of claim 7 is allowed to act on the fungi, plants or seed threatened by fungus attack.

10. A fungicidal composition according to claim 3, wherein in the formula I $R^1$ is cyclohexyl and $R^2$ is 2-chlorophenyl, in trans configuration.

11. A fungicidal composition according to claim 3, wherein in the formula I $R^1$ is cyclohexyl and $R^2$ is 4-chlorophenyl, in trans configuration.

12. A process of combating fungi according to claim 4, wherein in the formula I $R^1$ is cyclohexyl and $R^2$ is 2-chlorophenyl, in trans configuration.

13. A process of combating fungi according to claim 4, wherein in the formula I $R^1$ is cyclohexyl and $R^2$ is 4-chlorophenyl, in trans configuration.

* * * * *